(12) United States Patent
Crawford et al.

(10) Patent No.: US 6,673,047 B2
(45) Date of Patent: Jan. 6, 2004

(54) BLOOD COLLECTION SET

(75) Inventors: Jamieson William Maclean Crawford, New York, NY (US); Stefanie Livanos, Bethlehem, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 163 days.

(21) Appl. No.: 10/054,475

(22) Filed: Nov. 13, 2001

(65) Prior Publication Data

US 2002/0188256 A1 Dec. 12, 2002

Related U.S. Application Data

(60) Provisional application No. 60/260,173, filed on Jan. 5, 2001.

(51) Int. Cl.[7] .............................................. A61M 5/32
(52) U.S. Cl. ................. 604/177; 604/110; 604/164.08
(58) Field of Search .............................. 604/110, 523, 604/165.01–165.04, 167, 171, 174, 175, 177, 187, 192, 195, 198, 162, 164.04, 164.08, 158

(56) References Cited

U.S. PATENT DOCUMENTS

| | | |
|---|---|---|
| 4,813,940 A | 3/1989 | Parry |
| 5,330,438 A | 7/1994 | Gollobin et al. |
| 5,498,241 A | 3/1996 | Fabozzi |
| 5,899,886 A | 5/1999 | Cosme |

FOREIGN PATENT DOCUMENTS

| | | |
|---|---|---|
| EP | 0409180 A1 | 1/1991 |
| WO | WO 98/42393 | 10/1998 |

*Primary Examiner*—Brian L. Casler
*Assistant Examiner*—Michael M Thompson
(74) *Attorney, Agent, or Firm*—Nanette S. Thomas, Esq.; Scott J. Rittman, Esq.

(57) ABSTRACT

An automatically shieldable blood collection set is provided. The blood collection set includes a needle assembly having a hub with inner and outer tubes. A needle cannula is fixedly attached to the inner tube. The outer tube is split longitudinal, and a first spring biases the slit into an open orientation. A safety shield is telescoped between the tubes to the hub and the needle cannula and can be moved from a proximal position where the needle cannula is exposed to a distal position where the needle cannula is safely shielded. A second spring is provided between the shield and the hub to propel the shield distally relative to the hub and into surrounding relationship with the needle cannula. However the outer tube can be biased against forces of the first spring to slit and clamp the shield in a fixed position.

5 Claims, 1 Drawing Sheet

BLOOD COLLECTION SET

This application claims the benefit of provisional application Ser. No. 60/260,173 filed Jan. 5, 2001.

BACKGROUND OF THE INVENTION

1. Field of the Invention

The subject invention relates to a blood collection set having a needle cannula and a shield that can be driven forwardly to safely shield the needle cannula.

2. Description of the Related Art

A prior art blood collection set includes a small diameter needle cannula having a pointed distal end and a proximal end mounted to a thermoplastic hub. Portions of the blood collection set near the hub may be provided with a pair of flexible wings. The wings can be folded into face-to-face engagement with one another to facilitate digital manipulation of the small needle cannula. The wings then can be folded away from one another and taped into face-to-face engagement with the skin of the patient near a puncture site. The prior art blood collection set further includes a flexible plastic tube that has one end connected to the hub and an opposed end connected to a fitting. The fitting can be placed in communication with a reservoir to which collected blood may be directed.

The needle cannula of the prior art blood collection set typically is shielded prior to and after use to prevent accidental sticks. Needle shields used with prior art blood collection sets have taken many forms. Typically, a prior art blood collection set is packaged with a rigid tubular cap telescoped over the needle cannula to prevent accidental sticks prior to use. This tubular cap is removed from the needle cannula immediately prior to use of the blood collection set. Most prior art blood collection sets further include a second shield that is telescoped over the needle cannula and hub. The second shield may include at least one slot through which wings of the prior art hub may extend. Thus, the medical technician who uses the prior art blood collection set will hold the wings of the needle hub in one hand and the shield in the other hand after removing the needle cannula from the patient or blood donor. The wings then are slid proximally relative to the shield, thereby drawing the needle cannula into the shield. Some prior art shields are configured to engage the wings when the needle cannula has been shielded to make a re-exposure of the needle cannula difficult.

The digital manipulation that is required to shield the used needle cannula of a prior art blood collection set creates the potential for generating the accidental needle stick that the shield is intended to avoid. In particular, it is undesirable to rely upon a shielding that requires two hands to be moved in opposite directions in proximity to the point of a used needle cannula. Accordingly, the inventors herein have recognized the desirability of providing an automatically shieldable needle cannula for a blood collection set.

SUMMARY OF THE INVENTION

The subject invention relates to a blood collection set which comprises a needle cannula having a proximal end, a pointed distal end and a lumen extending therebetween.

The blood collection set further includes a hub that may be molded from a thermoplastic material. The hub includes proximal and distal ends. Additionally, the hub includes inner and outer tubes extending between the proximal and distal ends. The inner and outer tubes are connected to one another at the proximal end of the hub. However, the inner and outer tubes are spaced from one another at all other locations to define a cylindrical space that is open at the distal end of the hub. The outer tube of the hub includes a longitudinal slit extending continuously between the proximal and distal ends. Additionally, the outer tube includes a pair of transverse wings extending outwardly near the distal end of the hub. Biasing means is provided for urging the slit open. However, the wings can be deflected toward one another and against the force of the slit biasing means. Movement of the wings toward one another closes the slit, while movement of the wings away from one another in response to forces of the slit biasing means opens the slit. The slit biasing means may be a separate spring extending between the wings. Alternatively, the slit biasing means may rely, at least in part, on the inherent resiliency of the outer tube of the hub. The passage extends continuously through the inner tube from the proximal end of the hub to the distal end. The distal end of the inner tube of the hub is securely mounted to the proximal end of the needle cannula. Thus the lumen through the needle cannula communicates with the passage through the inner tube of the hub.

The blood collection set may further include a length of flexible tubing having opposed proximal and distal ends. The distal end of the flexible tubing may be connected to the proximal end of the hub such that the lumen through the needle cannula and the passage through the hub both communicate with the passage through the flexible tubing. The flexible tubing further includes a proximal end that may be connected to a fitting. The fitting may comprise a needle cannula that enables the blood collection set to be placed in communication with a reservoir for receiving a sample of blood. The tubing and the fitting may be of conventional design.

The blood collection set may further include a substantially rigid generally tubular safety cap mounted over the needle cannula for protection against accidental needle sticks prior to use of the blood collection set. The safety cap may include a proximal end that is frictionally engaged with the hub. The rigid tubular safety cap may be removed immediately prior to use of the blood collection set.

The blood collection set further includes a safety shield that is telescoped in the cylindrical space between the inner and outer tubes of the hub. The safety shield is moveable from a proximal position, where the needle cannula is exposed, to a distal position, where the needle cannula is safely shielded. Shield biasing means are provided between the shield and the hub for urging the shield to the distal position. The shield biasing means may be a coil spring that surrounds a portion of the hub. The safety shield is dimensioned to move in the cylindrical space between the inner and outer tubes of the hub only when the outer tube of the hub is biased into a position where the longitudinal slit is open. However, movement of the wings toward one another closes the slit and prevents axial movement of the shield relative to the hub and the needle cannula.

The needle assembly is used by positioning the shield in the proximal position and against the force of the shield biasing means. The wings then are squeezed together to close the slot and hold the shield in the proximal position. The needle assembly then can be used in a conventional manner. After use, the wings are released and resiliently return to their initial position. This resilient movement of the wings opens the slot and enables the shield to be propelled distally under the force of the shield biasing means.

DETAILED DESCRIPTION

Figure 1:
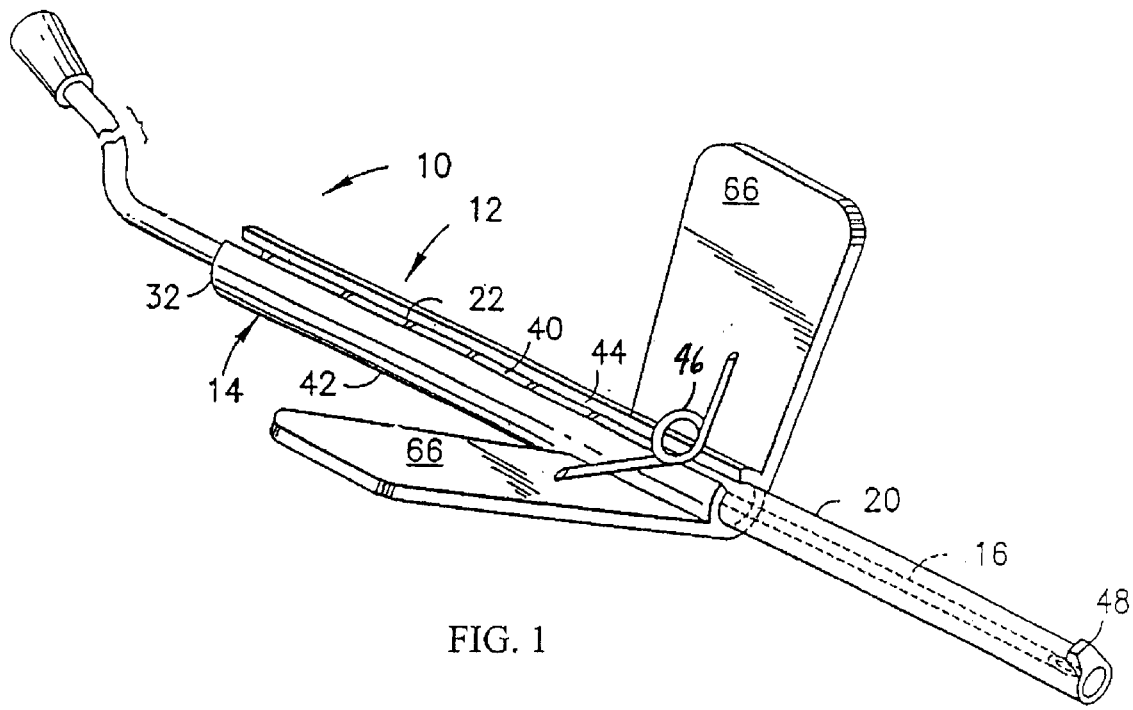
FIG. 1 is a perspective view of a needle assembly in accordance with the subject invention.
Figure 2:
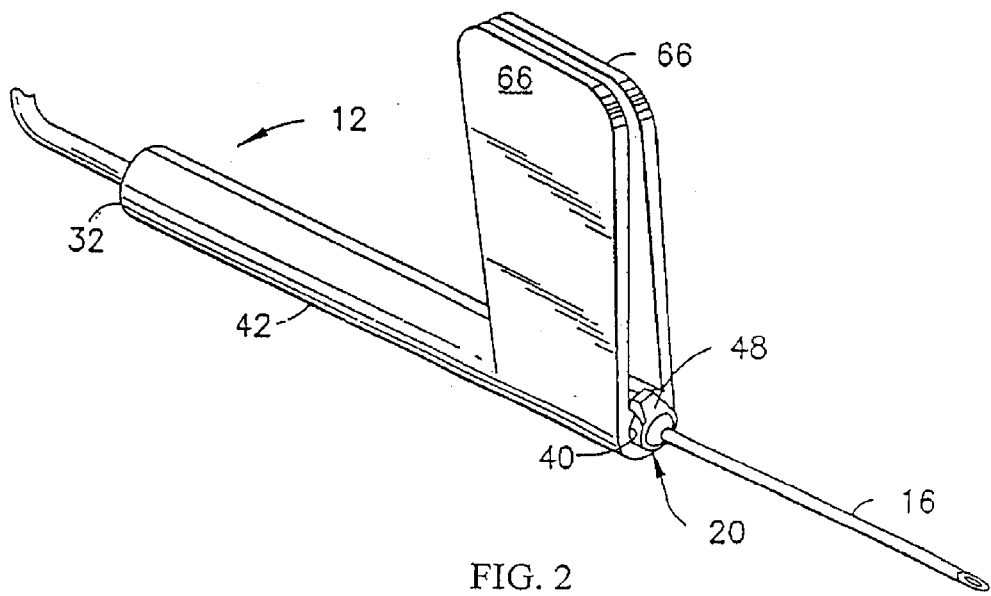
FIG. 2 is a perspective view similar to FIG. 1, but showing the needle assembly in the ready to use condition.

A blood collection set in accordance with the subject invention is identified by the numeral 10 in FIGS. 1 and 2.

Blood collection set 10 includes a needle assembly 12 which comprises a needle hub 14, a needle cannula 16, a needle shield 20 and a first spring 22. Hub 14 includes a proximal end 32, and a distal end 34. A tubular inner wall 40 extends substantially from proximal end 32 to distal end 34 and has a passage extending therebetween. The passage extending through tubular inner wall 40 of hub 14 communicates with the lumen extending through needle cannula 16.

Hub 14 further includes an outer wall 42 connected or longitudinally fixed relative to inner wall 40. Outer wall 42 is provided with a longitudinal slit 44 extending entirely therealong. Wings 66 extend transversely from outer wall 42 on opposite sides of slit 44. Additionally, a second spring 46 extends between wings 66. Second spring 46 is operative for urging wings 66 away from one another, and thereby opening slit 44 as shown in FIG. 1. However, wings 66 can be urged toward one another and against forces exerted by second spring 46. Movement of wings 66 into the FIG. 2 orientation closes slit 44, and thereby reduces the inside diameter of outer wall 42.

Shield 20 is an elongate substantially tubular member that is telescoped over inner wall 40 of needle hub 14 and over needle cannula 16. Shield 20 has an outside diameter less than the inside diameter defined by outer wall 42 when slit 44 is open. However, the outside diameter of shield 20 exceeds the inside diameter of outer wall 42 when wings 66 are urged toward one another to close slit 44. Shield 20 is provided with a radial projection 48 at the distal end of shield 20. Spring 22 is disposed between inner wall 40 and outer wall 42 and between proximal end 32 of hub 14 and shield 20.

Needle assembly 12 differs from the prior needle assemblies in that a separate safety cap is not provided. Rather, shield 20 is in a protective shielding position around needle cannula 16 prior to use of needle assembly 12. Needle assembly 12 is placed in condition for use by applying proximal forces on radial projection 48 to urge shield 20 proximally relative to hub 14. Shield 20 is releasably retained in a retracted position merely by squeezing wings 66 toward one another to close slit 44 and thereby reduce the inside diameter of outer wall 42. The reduced diameter effectively retains shield 20 in the proximal position while needle cannula 16 is being inserted into the patient. After insertion of needle cannula 16 into the patient, wings 66 can be relaxed. Second spring 46 then urges wings 66 away from one another, thereby widening slit 44 and increasing the inside diameter of outer wall 42. Thus, while needle cannula 16 is still in the patient, shield 20 will advance toward the puncture site. As needle cannula 16 is withdrawn from the patient, first spring 22 will continue urging shield 20 distally and into shielding engagement around needle cannula 16. Thus, needle assembly 12 provides for automatic and passive shielding.

What is claimed is:

1. A needle assembly comprising:
   a needle cannula having opposed proximal and distal ends and a lumen extending therebetween;
   a hub having opposite proximal and distal ends, an inner ate with a passage extending between said proximal and distal ends of said hub, portions of said inner tube at said distal end of said hub being connected to said proximal end of said needle cannula such that the lumen through the needle cannula communicates with the passage through the inner tube, an outer tube surrounding the inner tube, a longitudinal slit extending through said outer tube from said proximal end to said distal end of said hub, the outer tube further comprising a pair of transverse wings disposed on opposite respective sides of the slit, the wings being deflectable toward one another for deflecting said outer tube into a position for narrowing said slit, a cylindrical space between said inner and outer tubes and extending proximally from said distal end of said hub;
   a first biasing element engaging portions of said outer tube on opposite respective sides of said slit, for widening said outer tube at said slit and increasing cross-sectional dimensions of said cylindrical space;
   a shield disposed within outer tube of said hub and telescoped over said inner tube and said needle cannula, said shield being cross-sectionally dimensioned to be clamped in a fixed position by said outer tube when said outer tube is biased against forces of said first biasing element to close said slit, said shield further being dimensioned to move relative to said outer tube when said first biasing element biases said slit open;
   a second biasing element captured between said hub and said shield and being operative for propelling said shield from a proximal position where said needle cannula is exposed to a distal position where said needle cannula is shielded.

2. The needle assembly of claim 1, wherein the first biasing element extends between said wings of said outer tube.

3. The needle assembly of claim 1, wherein the shield has opposed proximal and distal ends, the second biasing element being a spring extending between the proximal end of the shield and the proximal end of the hub.

4. The needle assembly of claim 1, wherein the inner and outer tubes of the hub are connected to one another at a location substantially diametrically opposite said slit.

5. The needle assembly of claim 1, further comprising a flexible tube connected to and extending from the proximal end of the hub, such that a passage through a flexible tube communicates with the passage through the inner tube of the hub.

* * * * *